(12) United States Patent
Magnusson et al.

(10) Patent No.: US 9,155,665 B2
(45) Date of Patent: Oct. 13, 2015

(54) MENSTRUAL TAMPON

(75) Inventors: Ulla Magnusson, Mölniycke (SE); Monica Kjellberg, Partille (SE); Craig Doyle, Melbourne (AU); Oscar Lipschutz, Göteborg (SE); Britt-Marie Wiezell, Möinlycke (SE); Conny Dahlqvist, Lindome (SE); Trudy Balchin, Camberwell (AU)

(73) Assignee: SCA HYGIENE PRODUCTS AB, Göteborg (SE)

( * ) Notice: Subject to any disclaimer, the term of this patent is extended or adjusted under 35 U.S.C. 154(b) by 671 days.

(21) Appl. No.: 13/258,504

(22) PCT Filed: Jun. 29, 2009

(86) PCT No.: PCT/SE2009/050831
§ 371 (c)(1),
(2), (4) Date: Sep. 22, 2011

(87) PCT Pub. No.: WO2011/002357
PCT Pub. Date: Jan. 6, 2011

(65) Prior Publication Data
US 2012/0089111 A1    Apr. 12, 2012

(51) Int. Cl.
*A61F 13/20* (2006.01)

(52) U.S. Cl.
CPC ......... *A61F 13/2051* (2013.01); *A61F 13/2031* (2013.01); *A61F 13/2034* (2013.01); *A61F 13/2037* (2013.01); *A61F 13/2077* (2013.01)

(58) Field of Classification Search
CPC ............ A61F 13/2031; A61F 13/2034; A61F 13/2051; A61F 13/2077; A61F 13/20; A61F 13/34

USPC ....................... 604/385.18, 379, 11
See application file for complete search history.

(56) References Cited

U.S. PATENT DOCUMENTS 2,499,414 A * 3/1950 Rabell ........................... 604/377
3,058,486 A * 10/1962 McDermott et al. ....... 137/515.5

(Continued)

FOREIGN PATENT DOCUMENTS

CN      101378711 A      3/2009
DE     103 06 678 A1     8/2004

(Continued)

OTHER PUBLICATIONS

Office Action (Notification of the First Office Action) issued on Dec. 18, 2013, by the State Intellectual Property Office of the People's Republic of China in corresponding Chinese Patent Application No. 200980160150.6, and an English Translation of the Office Action. (19 pages).

(Continued)

*Primary Examiner* — Susan Su
(74) *Attorney, Agent, or Firm* — Buchanan Ingersoll & Rooney PC (57) ABSTRACT

The disclosure concerns a compressed menstrual tampon including an elongated generally rod-shaped absorption body having an insertion end and a withdrawal end and having a withdrawal string extending from the withdrawal end. The absorption body has at least one wave-shaped compression line extending continuously from the insertion end to the withdrawal end.

25 Claims, 9 Drawing Sheets

(56) References Cited

U.S. PATENT DOCUMENTS

| | | | |
|---|---|---|---|
| 4,175,561 A * | 11/1979 | Hirschman | 604/385.17 |
| 4,755,166 A * | 7/1988 | Olmstead | 604/11 |
| 5,374,258 A * | 12/1994 | Lloyd et al. | 604/358 |
| 5,592,725 A | 1/1997 | Brinker | |
| D477,075 S * | 7/2003 | Schoelling | D24/125 |
| D485,354 S * | 1/2004 | Carlin et al. | D24/125 |
| 7,087,045 B2 | 8/2006 | Jensen | |
| 7,214,218 B2 * | 5/2007 | Carlin | 604/385.17 |
| 7,338,483 B2 * | 3/2008 | Carlin et al. | 604/385.17 |
| 7,549,982 B2 * | 6/2009 | Carlin | 604/385.18 |
| 7,967,803 B2 * | 6/2011 | Van Ingelgem et al. | 604/385.17 |
| 8,023,385 B2 * | 9/2011 | Jung | 369/103 |
| 8,029,485 B2 * | 10/2011 | Jensen | 604/385.17 |
| 8,460,262 B2 * | 6/2013 | Fung et al. | 604/385.18 |
| 8,574,210 B2 * | 11/2013 | Van Ingelgem et al. | 604/385.17 |
| 2002/0151859 A1 | 10/2002 | Schoelling | |
| 2003/0023214 A1 | 1/2003 | DiSalvo et al. | |
| 2003/0229328 A1 | 12/2003 | Costa | |
| 2004/0030280 A1 * | 2/2004 | Mercier | 604/11 |
| 2005/0113782 A1 | 5/2005 | Carlin | |
| 2005/0113783 A1 * | 5/2005 | Carlin et al. | 604/385.18 |
| 2005/0113787 A1 * | 5/2005 | Carlin | 604/385.18 |
| 2005/0113788 A1 | 5/2005 | Carlin | |
| 2005/0113807 A1 | 5/2005 | Carlin | |
| 2005/0143708 A1 * | 6/2005 | Hagberg et al. | 604/385.18 |
| 2006/0167430 A1 * | 7/2006 | Denti et al. | 604/385.17 |
| 2006/0200103 A1 | 9/2006 | Schmidtbauer et al. | |
| 2007/0083182 A1 * | 4/2007 | Schoelling | 604/385.18 |
| 2008/0154222 A1 | 6/2008 | Chaffringeon | |
| 2008/0200892 A1 * | 8/2008 | Van Ingelgem et al. | 604/379 |
| 2009/0024103 A1 | 1/2009 | Van Ingelgem et al. | |
| 2011/0238028 A1 * | 9/2011 | Smet | 604/385.17 |
| 2012/0283684 A1 * | 11/2012 | Schmidt-Foerst et al. | 604/385.17 |

FOREIGN PATENT DOCUMENTS

| | | |
|---|---|---|
| DE | 10 2005 050 514 A1 | 4/2007 |
| EP | 1 459 720 A1 | 9/2004 |
| EP | 1 481 656 A1 | 12/2004 |
| EP | 1 547 554 A1 | 6/2005 |
| EP | 1 547 555 A1 | 6/2005 |
| RU | 2005 131 426 A | 2/2006 |
| RU | 2 338 498 C2 | 11/2008 |
| WO | 95/03766 A2 | 2/1995 |
| WO | 01/43679 A1 | 6/2001 |
| WO | 02/076357 A2 | 10/2002 |
| WO | 02/078586 A2 | 10/2002 |
| WO | 04/000184 A1 | 12/2003 |
| WO | 2004/028428 A1 | 4/2004 |
| WO | 2004/080362 A1 | 9/2004 |
| WO | 2004/085720 A1 | 10/2004 |
| WO | 2007/001216 A1 | 1/2007 |
| WO | 2007/088057 A1 | 8/2007 |
| WO | 2008/062322 A2 | 5/2008 |
| WO | 2008/095937 A2 | 8/2008 |
| WO | WO 2012/150515 A2 * 11/2012 ............. A61F 13/15 |  |

OTHER PUBLICATIONS

Office Action (Decision on Grant) dated Aug. 26, 2013, issued by the Russian Patent Office in the corresponding Russian Patent Application No. 2012102928 and an English translation thereof. (13 pages).

Extended European Search Report dated Mar. 4, 2013, issued by the European Patent Office in the corresponding European Application No. 09846903.4. (9 pages).

Patent Examination Report issued in corresponding Australian Patent Application No. 2009348943, dated Jul. 5, 2013.

\* cited by examiner

MENSTRUAL TAMPON

TECHNICAL FIELD

The invention pertains to a compressed menstrual tampon comprising an elongated generally rod-shaped absorption body having an insertion end and a withdrawal end and having a withdrawal string extending from the withdrawal end.

BACKGROUND ART

Menstrual tampons for intra-vaginal use have long been in use and are favoured by many women as they are considered to be hygienic, non-obtrusive and comfortable to wear, lacking the occluding plastic backing of external protection devices such as sanitary napkins. A further advantage is that tampons are discrete and can be used with swimwear and other tight-fitting garments without being visible from the outside.

Tampons are commonly made from absorbent fibres, usually cellulosic fibres such as cotton fibres or regenerated cellulose fibres, such as viscose. It is also known to include other absorbent materials such as absorbent foams and superabsorbent gelling materials in tampons and also non-absorbent materials such as non-absorbent fibres, binders and fillers.

In order to better utilise the absorption material it has been suggested to provide tampons with external grooves or channels in order to increase the surface of the tampon that will be available for absorption. These grooves or channels may be formed by compression of the tampon body and may be arranged in a spiral configuration or may run as straight from the top of the tampon to the withdrawal end as described in WO 2002/078586, WO 2002/076357, WO 95/03766 and WO 2004/028428. However, it has been found that even when provided with such grooves or channels, users still experience a problem with fluid leaking out past the tampon. Such leakage often occurs prematurely, before the tampon has been fully saturated with liquid.

WO 2008/062322 A2 discloses a sanitary tampon that has been impregnated with a hydrophobic substance in order to counteract expansion and absorption in the treated end zone of the tampon. The hydrophobic substance is said to limit leakage and facilitating withdrawal of the tampon after it has been used. However, for several reasons it is highly desirable to avoid any additives to a tampon as any substance that will be in contact with the mucosal tissues may potentially cause problems with irritation and allergy. Additional components in a disposable article such as a tampon will also increase the production cost both by complicating the production process and by adding to the material cost. Moreover, the hydrophobic substance will negatively affect the absorbent capacity of the tampon by blocking the capillary structure in the tampon and by limiting the expansion capacity of the tampon.

Accordingly, it is an object of the present invention to provide a menstrual tampon having improved ability to prevent premature leakage.

SUMMARY

The disclosure relates to a compressed menstrual tampon comprising an elongated generally rod-shaped absorption body having an insertion end and a withdrawal end and having a withdrawal string extending from the withdrawal end. The absorption body of the tampon according to the invention has at least two wave-shaped compression lines extending from the insertion end to the withdrawal end.

It has been found that even when a tampon has a theoretical absorbent capacity that would be expected to be sufficient to prevent leakage of liquid during use of the tampon, liquid may anyway escape past the tampon by running in rugosities on the vaginal wall and eventually leaking out without being absorbed by the tampon. This is an effect of the vagina not having a perfect tubular shape with a circular cross section. Instead, the vaginal wall is wrinkled and the vagina has a flattened shape with a central channel having an H-shaped cross section. Accordingly, the prior art tampons with a regular generally cylindrical cross section will only fill out the central portion of the vagina, leaving longitudinal channels in the vaginal wall in which fluid may run without being intercepted by the tampon.

By providing the tampon with grooves in the form of wave shaped compression lines, the tampon has an irregular shape that better conforms to the irregularities in the vaginal wall in particular when the tampon absorbs liquid and swells. Thereby, the tampon provides improved leakage inhibition. By arranging the wave shaped compression lines in a non-congruent pattern, liquid distribution in the tampon may be controlled and a non-uniform distribution pattern may be obtained in the tampon body. A non-congruent pattern of wave shaped compression lines is a pattern where neighbouring wave shaped compression lines or segments of a spiralling compression line are offset so that the wave-crests and wave-throughs are non-aligned. A non-congruent pattern is obtained when wave shaped compression lines or wave shaped line segments having uniform and equal wave-lengths are offset by a portion of a wave-length such as by half a wave-length. A non-congruent pattern may also be obtained when different wave-lengths are used in one and the same wave shaped compression line or when the wave shaped compression lines or wave shaped line segments have non-varying but mutually different wave-lengths. When more than one wave shaped compression line is used, the compression lines may differ in wave amplitude, wavelength, impression depth and/or may have the waves shifted longitudinally in relation to each other so that the waves in neighbouring wave shaped compression lines are out of phase with each other.

The wave shaped compression lines form grooves in the tampon body that are relatively denser liquid-absorbent structures acting to draw liquid into the absorption body. The grooves will also act as channels for liquid running on the surface of the tampon. The depth of the wave shaped compression lines may differ between the wave shaped compression lines and/or along one and the same wave shaped compression line so that the wave shaped compression line has a non-uniform density along its length. The depth of a groove formed by a wave shaped or straight compression line is the radial distance from the circumferential surface of the tampon to the radially innermost part of the groove. The depth of the compression lines may be of from 1 to 6 mm.

The wave shaped compression lines also give the tampon body an irregularly shaped outer surface that can swell in a non-uniform manner to fit against the irregularly shaped vaginal wall. The irregularly shaped outer surface of the tampon is well adapted to intercept and absorb menstrual fluid running on the vaginal wall before it may leak out past the tampon. The wave shaped compression lines may be hot compressed structures formed at elevated temperatures of 70° C. or more, that remain identifiable also after the absorption body has absorbed liquid. This means that the tampon largely retains the irregular and uneven outer surface also when the tampon is fully saturated, thus providing a higher degree of sealing against the vaginal wall. Alternatively, cold compression which is performed at temperatures below 70° C. may be used, allowing the wave shaped compression lines to be gradually obliterated or at least less prominent in the tampon body as the tampon swells to its full capacity. Combinations of hot compressed and cold compressed compression lines or portions of compression lines are also within the scope of the invention.

The wave shaped compression lines provide the tampon with an enlarged liquid receiving surface and constitute retardation means for liquid running in the channels formed by the wave shaped compression lines on the surface of the tampon. The wave shaped compression lines form longer liquid channelling paths prolonging the time during which liquid may be absorbed by the tampon.

The tampon is delivered to the user in a compressed state with the tampon body or "pledget" formed by compression into a bullet shape or rod shape. The tampon usually has a rounded, tapered, or flat tip at the insertion end and a flat generally circular withdrawal end surface at the withdrawal end. The insertion end is the part extending from the tip or upper end of the tampon one third of the length toward the withdrawal end surface or lower end of the tampon. Similarly, the withdrawal end is the part of the tampon extending from the withdrawal end surface one third of the tampon length toward the tip of the tampon. The compressed, unused tampon has a generally smooth, low friction body-contacting surface to facilitate comfortable insertion. The compressed structures such as wave shaped compression lines, indentations and dot compressions are clearly visible as impressions on the surface. As the tampon swells between the impressions, the irregular character of the tampon surface becomes gradually more pronounced.

The absorption body of the menstrual tampon may comprise a mass of fibres, preferably predominantly absorbent fibres or at least wettable fibres. The fibres may include cellulosic fibres such as rayon (viscose), cotton, and cellulose fluff pulp. The absorption body may also comprise binder material. Suitable binders include thermoplastic materials such as polyolefins, polyesters etc. and may be present as mono-component or multi-component fibres or in particle form. Further components in the absorption body may be non-absorbent fibres and fillers, odour control agents, pH regulating agents, etc. as known in the art.

It may be desirable to use absorption material with high absorption capacity in order to allow the tampons to be made smaller. The benefits of making the tampons smaller include reduced material costs, consumer preference to use smaller tampons, and savings and consumer preference for more compact packaging of the tampons.

In order to meet the demand for fibres having higher absorbency, multilimbed regenerated cellulosic fibres have been developed. Multilimbed viscose fibres have a cross-section with three or more lobes or limbs and are known to have higher absorbency than corresponding non-limbed viscose fibres. One example of viscose fibres having a triangular cross-section and improved absorbency is disclosed in WO 2004/085720.

The multilimbed regenerated cellulose fibres cannot readily be compressed into a state that ensures appropriate rigidity of the tampon. In order to be easy to manipulate and to insert into the vaginal cavity without collapsing, a tampon needs to have a minimum degree of rigidity. Excessive compression of multilimbed fibres may proportionally reduce the effective absorbency of the fibres. In order to overcome this problem, the multilimbed fibres may be blended with non-limbed viscose fibres or other non-limbed cellulosic fibres to achieve sufficient stability of the product. US 2002/0151859, US 2003/0229328, WO 01/43679 and WO 2004/000184 disclose tampon cores and the manufacture of tampon cores comprising blends of multilimbed fibres and non-limbed fibres.

A further possibility is to use different absorption materials for different parts of the absorption body such as an inner and outer body portion as disclosed in WO 2007/001216. When the outer body portion is predominantly made from multilimbed viscose fibres and the inner body portion is predominantly made from non-limbed cellulosic fibres, simultaneous compression of the inner and outer body portions will result in a tampon having a denser inner body portion and a less dense outer body portion. The material used in WO 2007/001216 is predominantly non-limbed cellulosic fibres such as non-limbed viscose fibres, cotton fibres or cellulose fluff pulp fibres for the inner body portion. Preferably, the non-limbed cellulosic fibres constitute at least 80% of the material in the inner body portion. The outer body portion may comprise at least 80% multi-limbed viscose fibres. The multilimbed fibres are preferably staple length fibres having at least three limbs and can have a Y-, X, H, or T-, cross-sectional shape with a symmetrical Y-shape being preferred.

When subjecting the inner and the outer body portions comprising non-limbed and multilimbed fibres as disclosed in WO 2007/001216 to simultaneous compression, the inner body portion will retain the compressed state to a greater degree than the outer body portion. The resiliency and low fibre-to-fibre friction of the multi-limbed fibres which make up the major part of the outer body portion will cause the outer body portion to spring back to a less compressed state.

The absorption body may comprise absorbent foam either as the only absorption material or in combination with fibres and optionally superabsorbent material. Foam-like fibrous structures such as disclosed in WO 99/61518 may also be used.

The absorption body may comprise or consist of superabsorbent material, i.e. material that is capable of absorbing liquid in amounts corresponding to many times their own weight. The superabsorbents may be in the form of superabsorbent foams, particles, fibres, flakes, granules, etc.

In order to facilitate insertion, the tampon may be bullet shaped with a rounded or tapering insertion end.

The wave-shaped compression lines may have an amplitude of from 0.3-5 mm, preferably from 0.5-3 mm. Sinusoidal waves with uniform amplitude and wave length are generally preferred from a manufacturing view. However, the waves may be of different amplitudes within the same wave shaped compression line and between different wave shaped compression lines. The compression lines may be formed with the same or different frequency between different wave shaped compression lines and with the waves aligned or offset in relation to each other. If the waves are offset so that the waves in different wave shaped compression lines are placed at non-equal distances from the insertion end, a spiralling flow pattern will be created inside the tampon. This will be the case also when the neighbouring wave shaped compression lines have a straight longitudinal compression line between them. Offset waves create a more irregular outer surface which is fully developed when the tampon has expanded after wetting.

The wave shaped compression lines may each have 1 to 6 full waves where each full wave comprises a wave crest and a wave trough. The wave length may be of from 5 to 50 mm, with at least one full wave length along each wave shaped compression line.

At least one of the wave shaped compression lines may have waves with different amplitudes. The waves within one and the same wave shaped compression line may also differ in wave-length.

In order to slow down liquid transport lengthwise in the tampon, the tampon may have 1-3 indentations at the withdrawal end. By slowing down liquid transport at the end, liquid will remain in the upper part of the tampon for a longer period of time. This allows for longer absorption times in the upper part of the tampon and better utilisation of the absorption material.

The indentations are compressed structures arranged circumferentially around the withdrawal end of the tampon. The indentations may be in the form of one or more wave-shaped or straight continuous ring-like line embossments or may be discontinuous, being made up of discrete embossments arranged to encircle the withdrawal end. When more than one indentation is arranged in the withdrawal end, the indentations may differ in shape, width, depth, impression angle, etc. The indentations may be cold compressed but are preferably hot compressed structures that remain visible and functional in the tampon also when the tampon is expanded after liquid absorption.

The distance between the withdrawal end surface and the proximal edge of the first indentation as seen from the withdrawal end is preferably 1-10 mm. The tampon may have at least two indentations placed at a distance from each other of from 1-7 mm. All indentations should be placed in the withdrawal end. In this context, the withdrawal end is considered to be the portion of the tampon closest to the withdrawal string and has a length that is one third of the total length of the tampon. The tampon length may be 30-70 mm, preferably 40-50 mm. Each indentation may have a width in the length direction of the tampon of 0.5-5 mm, preferably 1-4 mm.

The indentations may have a depth d from the tampon surface of from 0.5 to 4 mm, preferably of from 1 to 2 mm. When the indentations are wave-shaped or straight line impressions, the lines form troughs or channels in the tampon body. The troughs or channels may have straight walls parallel to the radial direction R of the tampon. However, preferably the walls are at an angle to the radial direction R of the tampon of from 0-60° with a rounded bottom surface. The inclination of the walls may be the same or different so that the trough may have a symmetrical or asymmetrical shape.

Indentations may be formed in a tampon with or without a liquid permeable cover on the outside of the absorption body of the tampon. Moreover, the indentations may be formed before providing the tampon with a protective, removable packaging cover, such as a cellophane film or after application of a packaging cover. In the latter case it at least one of the walls of the indentations can form an angle with the radial direction R of the tampon so that at least one of the walls is inclined in relation to the radial direction of the tampon.

The tampon may have at least one dot compression such as at least two dot compressions placed at the insertion end. In this context, the insertion end is considered to be the portion of the tampon closest to the tip and has a length that is one third of the total length of the tampon. The dot compressions are preferably of circular or oval shape and have a relatively small area in the order of 1-10 mm² and may have a depth of from 1 to 4 mm as measured from the surface of the tampon. The purpose of the dot compressions is to increase the liquid receiving surface at the tip of the tampon and to improve wicking into the tampon and thereby facilitate initial absorption of liquid into the absorbent core at the insertion end of the tampon. Liquid absorption triggers swelling of the absorption material and causes the insertion end of the tampon to be opened up thereby creating an increased liquid receiving surface.

The dot compressions may be hot compressed structures that remain in their compressed state in the tampon throughout its use. It is also conceivable to make the dot compressions at lower temperatures so that they are less stable structures that will be more or less obliterated as the tampon swells. This means that the initially densified material in the dot compressions can swell to its maximum capacity allowing greater total absorption in the tampon than had been the case if the dot compressions had remained in the expanded structure.

The wave shaped compression lines in the tampons may be made by hot compression or cold compression as found suitable.

In order to create stable, permanent compressed structures an elevated temperature will usually be required. Temperatures of 70° C. or more may be used in hot compression. As is well known by the person skilled in the art, other parameters of importance are the applied pressure, the pressing time and the composition of the material in the tampon. These parameters interact so that at higher temperatures shorter pressing times may be used. With commonly used tampon materials and pressing methods a temperature of around 100° C. and a forming time of 0.2-5 seconds may be suitable in order to obtain a stable compressed structure such as an indentation or a wave shaped compression line.

Cold compression, performed at temperatures below 70° C. and with relatively short pressing times results in compressed structures that may be less stable, implying that their impact on the swelling of the tampon will be less pronounced. Parameters such as pressing times, temperatures, and pressure may be selected as is known in the art in order to obtain the desired effect.

Hot compression may be used for the indentations for the reason that hot compressed structures will remain visible and functional for a longer time also after absorption although the swelling that takes place as the tampon absorbs fluid will affect the depth and definition of the compressed structures to some degree. Hot or cold compression may be used for dot compressions, as set out above. The dot compressions have an initial function in creating wicking passageways at the insertion end which allow the tampon to rapidly acquire liquid at the insertion end to promote expansion of the insertion end. The dot compressions have high capillarity and aid in guiding liquid into the tampon body. As liquid is absorbed and the tampon expands at the insertion end, the absorption body will expand and the dots will gradually loose their initial function. Cold compressed structures may be advantageous as they initially provide the material with a dense, wicking capillary structure allowing liquid to be sucked into the absorption body while subsequently allowing the absorbent material swell to its full capacity without being restricted by the compressed parts of the structure.

All conceivable combinations and degrees of cold compression and hot compression may be used to allow for initial good absorption and liquid wicking and transport of wicking along the absorption body while at the same time provide maximum absorption and swelling to fully utilize the absorption capacity of the absorbent material and to obtain a desired shape in the expanded tampon.

The tampon may have one or more straight and/or wave shaped compression lines that are made by cold compression and one or more straight and/or wave shaped compression lines that are made by hot compression. In this manner, the tampon will absorb in two steps; first by liquid wicking into the absorption body along and through the wave shaped compression lines and secondly by the cold compressed compression lines being gradually eliminated when the tampon absorbs liquid and expands. Liquid distribution in the tampon may be controlled by using compression lines with different depths along the length of the compression lines. When the tampon has more than one compression line, the depth of the compression lines may differ as well as the wave amplitudes, wavelength, etc. It is also possible to use non-congruent wave patterns with waves that are shifted between the grooves so that wave crests and wave troughs on neighbouring wave shaped compression lines are out of phase with each other. Non-congruent wave patterns enhance the irregular appearance of the tampon surface.

The tampon may have wave shaped compression lines alternating with straight compression lines. The compression lines may be arranged to extend from the insertion end to the withdrawal end with a general direction of extension that is parallel to the longitudinal direction L of the tampon. One or more wave shaped compression lines may be arranged to extend from the insertion end to the withdrawal end with a general direction of extension that deviates from the longitudinal direction L of the tampon so that the wave shaped compression line forms a spiralling pattern on the surface of the tampon. Combinations of compression lines deviating from the direction of the longitudinal direction of the tampon and compression lines arranged parallel with the longitudinal direction of the tampon are also conceivable. The compression lines may intersect to form a network of compression lines on the surface of the tampon body, with at least two of the compression lines being wave-shaped.

The tampon may have an equal number of wave-shaped compression lines and straight compression lines. The compression lines may be combined with one or more indentations placed at the withdrawal end. Likewise, one or more dot compressions may be arranged at the insertion end.

A liquid permeable outer cover may be arranged on the absorption body and the wave shaped compression lines may be formed in both the cover and the absorption body. The cover may comprise thermoplastic material that may be heated when compressions are formed in the tampon whereby the thermoplastic material melts or softens and serves as a binder for binding the cover to the tampon body and for stabilising the compressions. The compressions may be any of the compressed structures as disclosed herein, such as straight or wave shaped compression lines, indentations and dot compressions. The thermoplastic material may be polyolefins such as polyethylene and polypropylene, polyesters or mixtures of thermoplastic materials. The thermoplastic material may be in the form of film or fibres such as monocomponent or multicomponent fibres.

The cover is preferably a material that exhibits low friction to facilitate insertion and withdrawal of the tampon. The cover material may be arranged to cover all or part of the tampon body.

Suitable cover materials include those commonly known in the art.

BRIEF DESCRIPTION OF THE DRAWINGS

Embodiments of the invention will in the following be described in more detail, with reference to the figures that are shown on the appended drawings. In the drawings:

FIGS. 21 a-f show tampon pledgets having differently shaped and configured indentations at the withdrawal end.

FIGS. 22 a-b show tampons with combinations of different compressed structures.

DETAILED DESCRIPTION OF THE PREFERRED EMBODIMENTS

Figure 1:
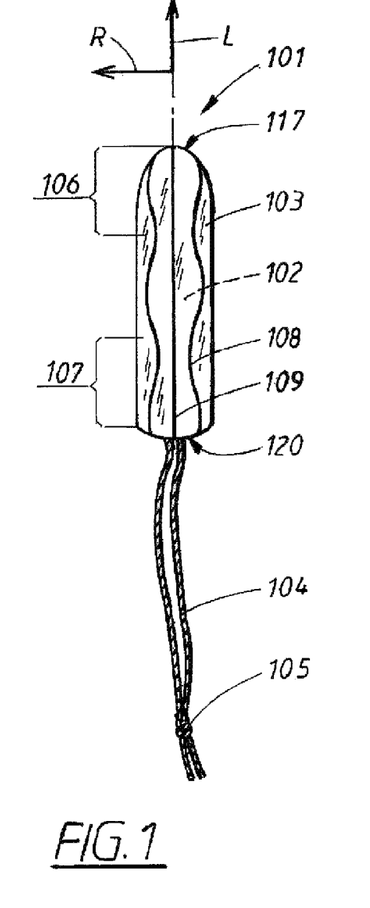
FIG. 1 shows a tampon having longitudinally extending wave shaped compression lines.
Figure 2:
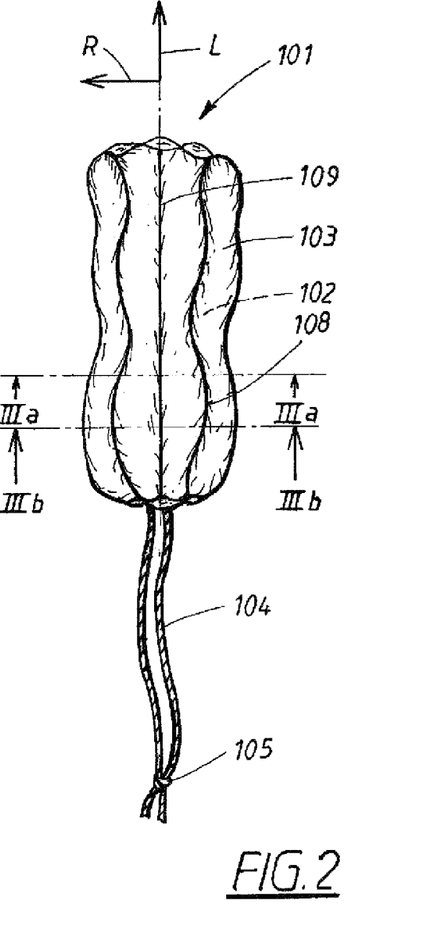
FIG. 2 shows the tampon in FIG. 1 in an expanded state after it has absorbed liquid, FIGS. 3 a,b shows cross-sections through the tampon in FIGS. 1 and 2 taken along the lines III a-III a and III b-III b in FIG. 2.

The tampon 101 shown in FIGS. 1 and 2 comprises an absorption body 102 enclosed in a liquid permeable cover 103 and having two withdrawal string ends 104 that are joined together in a knot 105. The tampon 101 has an elongate bullet-shape with a longitudinal direction L and a radial direction R, perpendicular to the longitudinal direction L and an insertion end 106 and a withdrawal end 107. Each of the insertion end 106 and the withdrawal end 107 occupy approximately one third of the total length of the tampon 101. The insertion end is shown with a rounded tip 117 and a flat withdrawal end surface 120. The tampon length between the tip 117 and the withdrawal end surface 120 may be determined by means of a slide calliper. Tampons commonly have a length in the dry, non-expanded state of from 30 to 70 mm, more common from 40 to 50 mm. The length will commonly vary with the size and design absorption capacity of the tampon.

The cover 103 may be any suitable non-abrasive liquid permeable material as is known in the art. Preferably, the cover 103 is a nonwoven material which may be a spun-bonded, carded or spunlaced web comprising polypropylene, polyethylene, viscose, bicomponent or any other suitable fibrous material. Perforated plastic films, cast, woven or knitted nettings or similar porous materials may also be used. The cover 103 is preferably hydrophilic. A hydrophilic cover material may be made from hydrophobic polymer materials and may be provided with a hydrophilic finish to render the cover wettable. The cover material may be applied to the entire tampon surface as is shown in FIGS. 1 and 2 or may be applied only to a part of the surface. It may, for example, be desirable to leave the tip of the tampon free from cover material.

The cover is an optional feature of the tampons and may be completely omitted, if desired. If no cover is used on the tampon, it is preferred that the absorption body be made of a material with sufficient integrity to avoid that fibres and/or particles are shed from the tampon during use.

The withdrawal string 104 is made from a material having high tensile strength and is firmly attached to the tampon body by being wound internally in the absorption body 102 or by being welded, glued or sewn to the absorption body 102 and/or to the liquid permeable cover 103. Usually two withdrawal string ends 104 such as shown in the Figs. are the ends of a single thread that is attached to the absorption body. The strings 104 may be joined by a knot 105 or the ends may be left free, as desired. Alternative designs with a single withdrawal string end protruding from the withdrawal end of the tampon are also conceivable within the scope of the invention. The withdrawal string 104 is preferably made from a non-absorbent and non-wicking material.

The absorption body 102 is preferably a mass of absorbent fibres that has been compressed into a generally cylindrical shape with a rounded insertion end 106, as shown in FIG. 1. However, other absorption materials such as foams and hydrogels may be used as well as non-absorbent components such as stabilising fibres, binders, antibacterial agents, etc. Mixtures and combinations of different absorbent and non-absorbent materials are within the scope of the invention, as herein described.

Figure 3A:
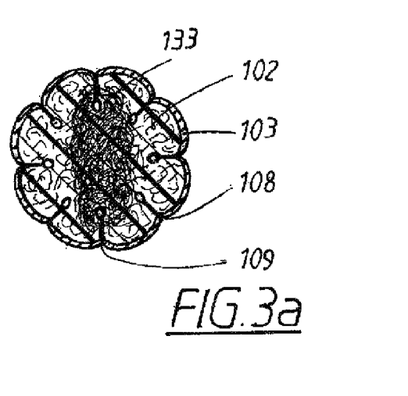
Figure 3B:
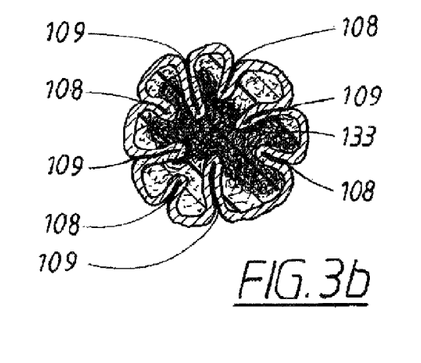

The tampon 101 is provided with longitudinally extending grooves or channels in the form of compression lines 108, 109. In the tampon shown in FIGS. 1-3, two sets of compression lines are pressed into the tampon. The first set of compression lines 108 have a sinusoidal wave shape and the second set of compression lines 109 are straight and extend parallel to the longitudinal direction L of the tampon. The wave-shaped compression lines 108 alternate with the straight compression lines 109 around the circumference of the tampon 101. In the embodiment shown in FIGS. 1-3, the tampon has four wave-shaped compression lines 108 or grooves and four straight compression lines 109 or grooves. Each wave-shaped compression line 108 is shown to have two full waves of equal length and with equal amplitude. Both the wave-length and the amplitude may be varied within the scope of the invention. The wave shaped compression lines are arranged in a non-congruent pattern, with neighbouring wave shaped compression lines 108 offset by a half wave length. The non-congruent wave patterns affect the liquid distribution in the tampon so that a non-uniform distribution spiralling distribution pattern is obtained in the tampon body. When more than one wave shaped compression line is used, the compression lines may differ in wave amplitude, wavelength and/or may have the waves shifted longitudinally in relation to each other so that the waves in neighbouring compression lines are out of phase with each other as shown in FIGS. 1-3a,b. As is indicated in FIGS. 3a and 3b, liquid applied to the tip of the tampon will travel downward in a spiralling pattern lengthening the way that the liquid travels before it reaches the withdrawal end 107. Eventually, the tampon will have reached its saturation and the spiralling liquid distribution pattern will gradually disappear as liquid fills all portions of the absorption material. In FIG. 3a which is a cross section taken at a location where the circumferential distance between neighbouring compression lines 108, 109 is approximately equal, the absorbed liquid is shown as a darkened area 133 running parallel to the height direction of the drawing page. In FIG. 3b which is a cross section taken at a location where the circumferential distance between neighbouring compression lines 108, 109 is at its maximum, the absorbed liquid is shown as a darkened area 133 that is tilted in relation to the height direction of the drawing page.

In the example shown in FIGS. 1-3, the straight compression lines 109 have different impression depth at different locations along the length of the compression lines 109. The impression depth in each straight compression line 109 varies in a wave pattern so that the impression depth is greatest at locations where the distance between the neighbouring wave shaped compression lines 108 is largest. This is indicated in FIG. 3b. The differing impression depths are optional to the FIG. 1-3 embodiment and to the other embodiments disclosed herein. The impression depth in the tampons may be from 1 to 6 mm.

Figure 4:
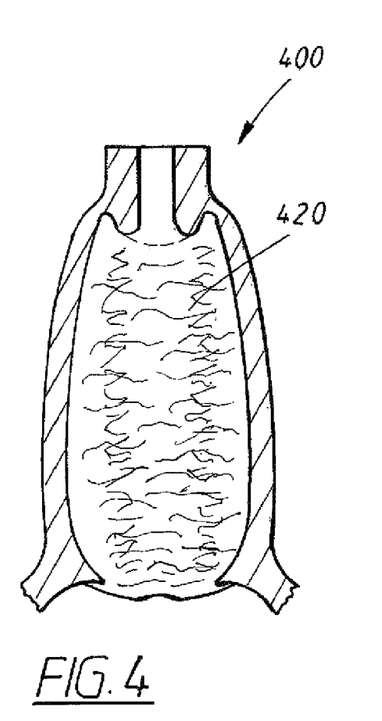
FIG. 4 shows a longitudinal section through the vagina
Figure 5:
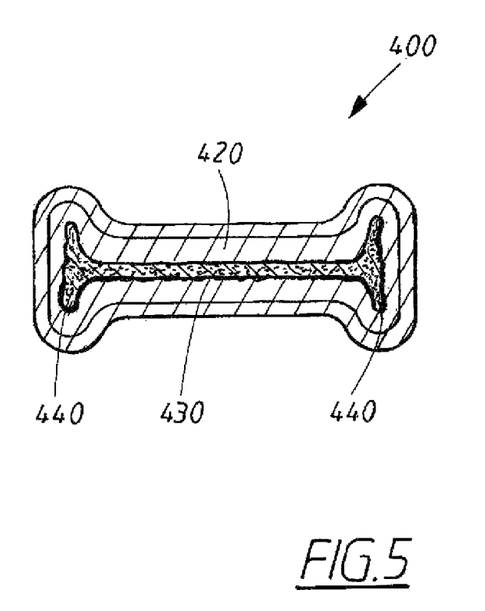
FIG. 5 shows a transverse section through the vagina.

FIG. 4 shows a longitudinal section through a vagina 400. The vagina is a 7-10 cm long muscular hollow organ connecting the outer female genitalia with the uterus. The vagina is located between the urinary bladder toward the front and the colon toward the back and is usually inclined somewhat to the rear at the upper portion. As is seen in FIG. 4, the vaginal wall is covered with mucosal tissue and has a wrinkled surface. FIG. 5 shows a cross-section through the vagina 400 and illustrates the non-circular appearance of the vagina with an H-shaped lumen 430. When a woman is menstruating, the flow of menstrual blood is not regular and constant but comes in sudden gushes. Menstrual blood may then run on the wrinkled vaginal wall 420 and in the longitudinal channels 440 at each side of the vagina 400.

When a tampon is inserted into the vagina, the efficiency of the tampon to prevent leakage depends on numerous parameters such as the total absorbent capacity of the tampon, the shape, surface area, liquid acquisition capacity and swelling rate, the placement of the tampon in the vagina, the ability of the tampon to intercept and block fluid flow in the vagina, the amount of fluid in each gush, the anatomy of the individual woman, the body position of the woman, etc. The tampon may have been non-centrally placed in the vagina or may have been leaning to one side. The depth to which the tampon is inserted in the vagina also plays an important role in how the tampon will function. Occasionally, the menstrual fluid does not impact the tampon at the tip as would be expected in an ideal case. Instead the menstrual fluid may impinge on the tampon somewhere along the length of the tampon body.

The tampon having wave-shaped compression lines 108 impressed therein has the ability to swell in a non-symmetrical and irregular way both in the circumferential direction and in the longitudinal direction. This allows the tampon to better adapt and conform to the irregular shape of the vagina and the vaginal wall. Due to the wave-shape in the compression lines, the distance between the compression lines varies along the length of the tampon. This in turn affects the ability of the absorption body to expand as compressed structures restrict expansion of the absorption material. It is preferred that at least some compression lines are made by heat pressing so that they remain as stable densified structures in the tampon also after absorption. However, it may also be desirable that one or more compression line is a structure formed at lower temperatures, such as below 70° C. and that will gradually loose its definition or even be completely obliterated when the absorption material swells. In this manner, the absorption body will reach a higher total absorption capacity than when all compression lines remain as well defined structures in the absorption body.

In addition to providing an irregular surface and a liquid channelling function, the wave-shaped compression lines enhance the ability of the tampon to catch premature leakage by providing an enlarged liquid receiving area and by leading liquid flowing on the tampon surface in a longer flow path.

Figure 6:
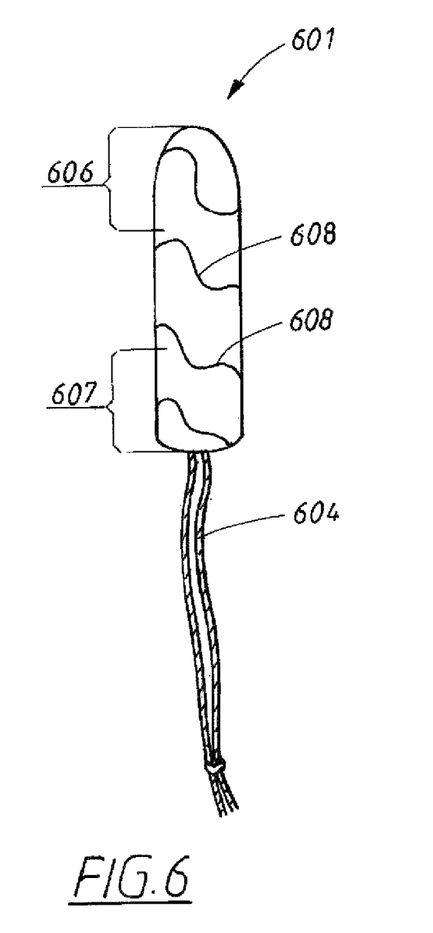
FIG. 6 shows a tampon having a spiralling wave shaped compression line extending from the insertion end of the tampon to the withdrawal end.
Figure 7:
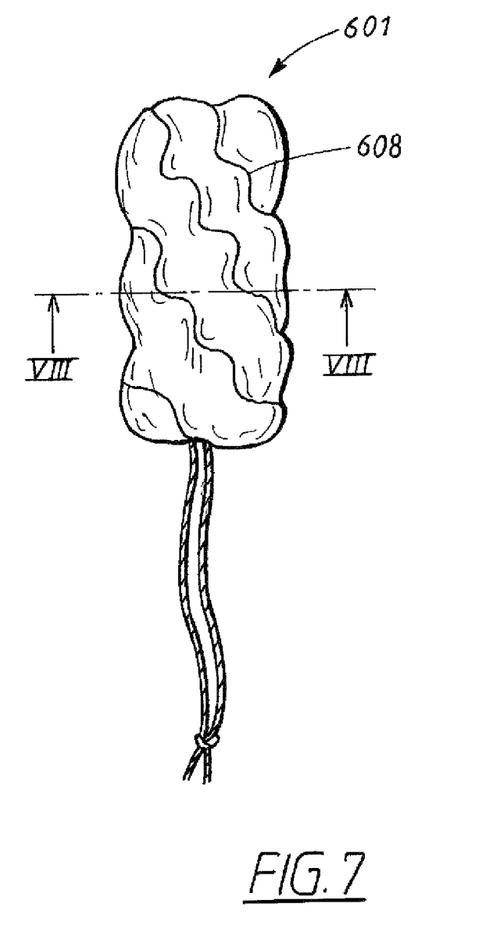
FIG. 7 shows the tampon in FIG. 6 in an expanded state after it has absorbed liquid.
Figure 8:
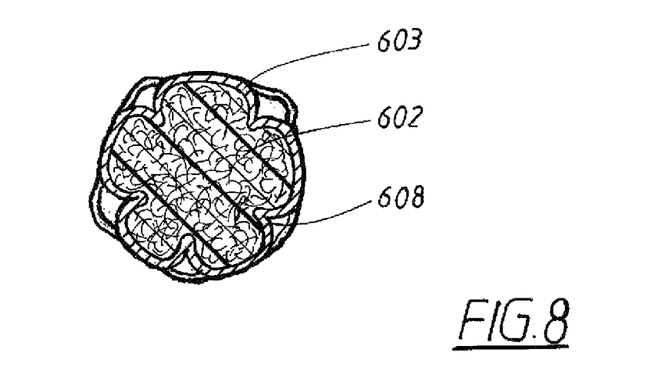
FIG. 8 shows a cross-section through the tampon in FIG. 7 taken along the line VIII-VIII.

FIG. 6 shows a compressed tampon in a dry state, before use. The tampon 601 has a single wave shaped compression line 608 arranged in a spiralling pattern from the insertion end 606 to the withdrawal end 607. The wavelength of the waves in the wave shaped compression line 608 is chosen so that the compression line forms a non-congruent pattern with waves in neighbouring windings being out of phase with each other, i.e. with the wave-crests and wave-troughs being offset between the windings. When the tampon absorbs menstrual fluid it will swell and acquire an irregular surface, as shown in FIG. 7 and in the cross-section in FIG. 8. When the tampon 601 is allowed to swell freely to saturation, it will have an appearance as shown in FIGS. 7 and 8. When the space available for expansion is restricted by the vaginal walls during use of the tampon, swelling will be correspondingly restricted when the tampon contacts the vaginal wall. Consequently, the irregular surface of the expanded tampon will shape itself to seal against the vaginal wall.

Figure 9:
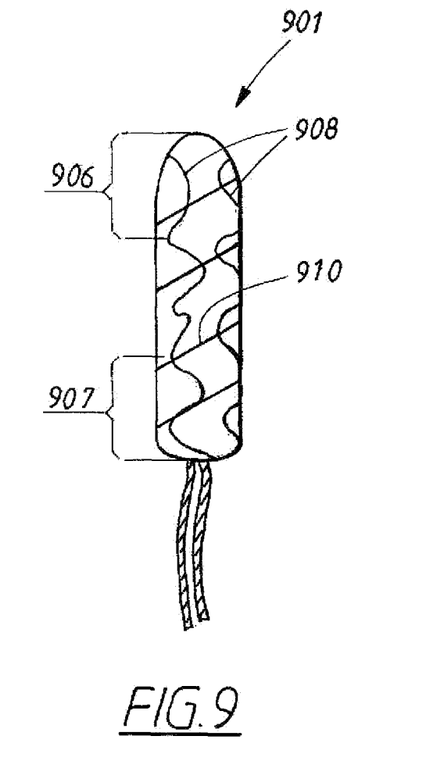
FIG. 9 shows a tampon having a combination of wave shaped compression lines and spiralling straight compression lines.
Figure 10:
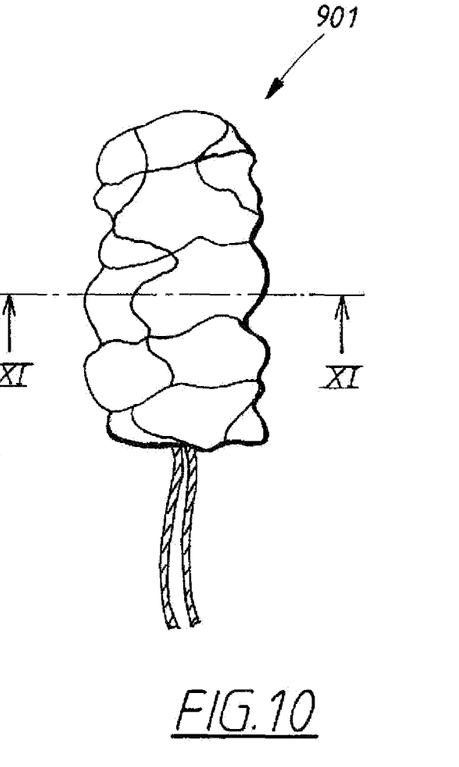
FIG. 10 shows the tampon in FIG. 9 in an expanded state after it has absorbed liquid.
Figure 11:
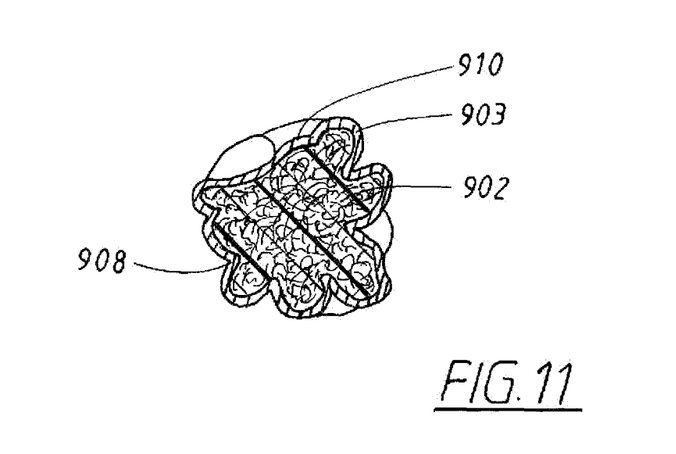
FIG. 11 shows a cross-section through the tampon in FIG. 10 taken along the line XI-XI.

A further example of a tampon 901 having wave-shaped compression lines 908 extending from the insertion end 906 to the withdrawal end 907 is shown in FIG. 9. In addition to the wave-shaped compression lines 908, the tampon 901 in FIG. 9 has a spiralling linear compression line 910 that also extends form the insertion end 906 to the withdrawal end 907 and that intersects with the wave-shaped compression lines 908. The wave-shaped compression lines 908 in FIG. 9 have a non-uniform wave-shape with varying wave amplitude and wave-length. When these non-uniform wave-shaped compression lines 908 are combined with a crossing compression line 910, the tampon acquires a highly irregular surface after swelling, as is shown in FIGS. 10 and 11.

Figure 12:
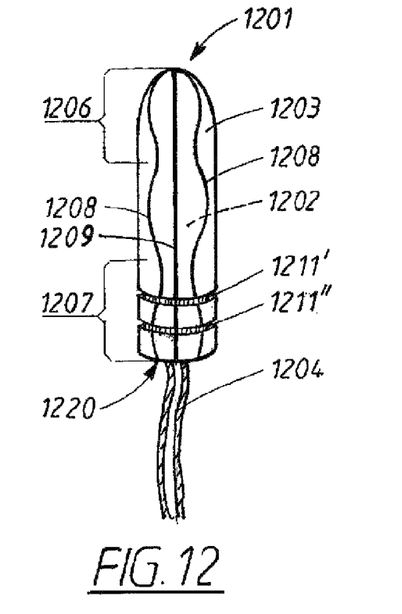
FIG. 12 shows a tampon having longitudinally extending wave shaped and straight compression lines and circular indentations in the withdrawal end.

The tampon 1201 shown in FIG. 12 has wave-shaped longitudinal compression lines 1208 and straight longitudinal compression lines 1209 in the same manner as in the tampon in FIGS. 1-3. In addition to the longitudinal compression lines 1208, 1209, the tampon 1201 in FIG. 12 has two indentations 1211', 1211", impressed in the withdrawal end 1207 of the tampon body. The indentations 1211', 1211" are shown as continuous ring shaped compression lines encircling the withdrawal end 1207 of the tampon. The indentations 1211', 1211" add to the irregular outer shape of the tampon body and constitute constrictions in the absorption body 1202 and the liquid permeable cover 1203 where the absorption material has been additionally densified. The densified portions of the absorption body 1202 have smaller capillaries that will slow down liquid flow toward the withdrawal end 1207 by promoting radial wicking of liquid at the level of each indentation and thereby constitute a barrier to leakage of liquid through the withdrawal end 1207. The indentations will also capture liquid running on surface of tampon and draw the liquid into the tampon in the dense absorbent structure created by the indentations.

Figure 13:
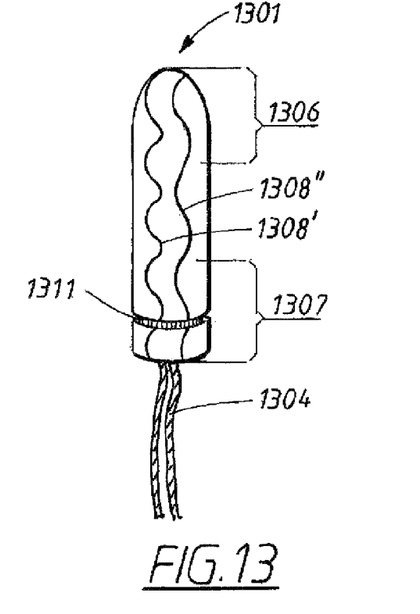
FIG. 13 shows a tampon having longitudinally extending wave shaped compression lines and one circular indentation in the withdrawal end.

In FIG. 13, the tampon 1301 has longitudinally extending wave shaped compression lines 1308', 1308" with different amplitudes and wave lengths. In addition, the tampon 1301 is shown to have a single indentation 1311, impressed in the withdrawal end 1307 of the tampon body in a manner similar to that of the indentations 1211', 1211" in FIG. 12.

The indentations 1211', 1211" and 1311 are shown as continuous ring formed compressed structures. However, the ring formed indentations may alternatively be formed as intermittent line compressions. It is also possible to use more than two ring shaped compressions placed at the withdrawal end of the tampon. The ring shaped compressions diminishes the total absorption capacity in the tampon by restricting expansion of the withdrawal end. For this reason, the compressions should only be placed in the withdrawal end 1207. The tampon may have up to 5 indentations but preferably not more than 1-3 indentations placed at the withdrawal end. The compressed structure in the indentations has high wicking capacity due to the dense structure and greater capillarity than surrounding parts of the absorbent structure. It may be desirable to place the first indentation as seen from the withdrawal end at a distance from the end surface 1220 of 1-10 millimeters. Thereby, the portion of the withdrawal end 1207 that is located closest to the withdrawal string 1204 will have a less dense and less wicking structure that will counteract fluid flow from the dense ring shaped indentation.

A further advantage of arranging indentations at the withdrawal end of the tampon is that the indentations will restrict the circumference of the withdrawal end, thereby facilitating easy withdrawal of the tampon.

If more than one indentation is used, at least two indentations may be placed at an edge-to-edge distance from each other of from 1-7 mm.

Figure 14:
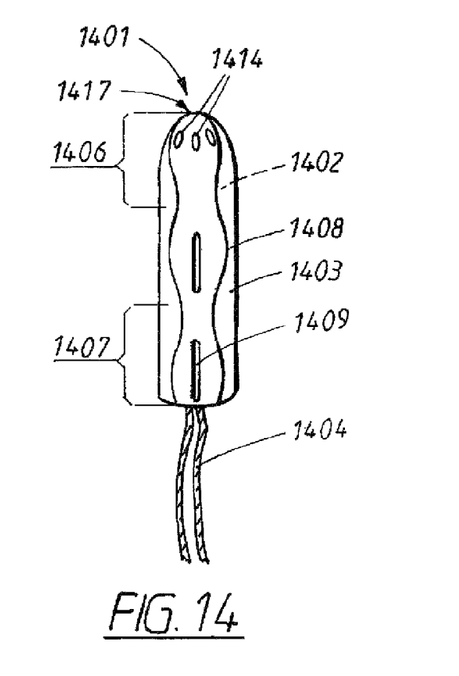
FIG. 14 shows a tampon having longitudinally extending wave shaped compression lines and dot compressions in the insertion end.
Figure 15:
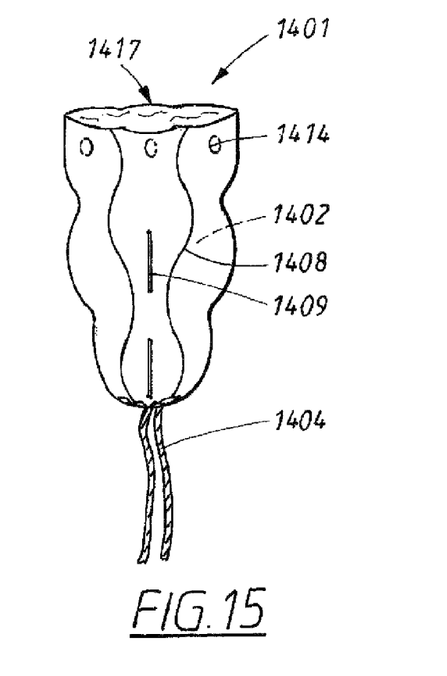
FIG. 15 shows the tampon in FIG. 13 after some initial absorption.

The tampon 1401 shown in FIG. 14 has longitudinally arranged wave shaped compression lines 1408 and longitudinally arranged compressed line segments 1409 placed radially between the wave shaped compression lines 1408. At the insertion end 1406 the tampon is provided with dot compressions 1414 arranged around the tampon tip 1417. When the tampon is wetted at the tip 1417, the dot compressions act as fluid passageways into the absorption body 1402 and increase reception area by providing a more irregular surface structure that will better capture liquid. The fluid reaching the absorption body 1402 causes the absorption material to absorb liquid and start to swell so that the tampon tip is opened up as shown in FIG. 15 to present an enlarged liquid receiving surface for fluid that subsequently impinges on the tampon tip 1417.

The dot compressions 1414 would typically be hot pressed structures but may be cold pressed structures that are less stable than compressed structures formed using heat. The dot compressions 1414 need only be present initially when the tampon first starts to absorb liquid. After the tampon has been opened up, the dot compressions may disappear as the tampon body expands to its full capacity. The dot compressions may be made before or after application of permeable surface layer.

Figure 16:
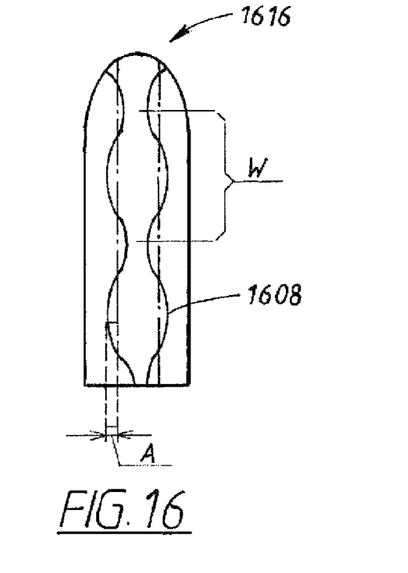
FIG. 16 shows how wave amplitude and wavelength are determined in wave shaped compression lines.

The compressed tampon pledget 1616 in FIG. 16 is shown without a withdrawal string and has two longitudinally extending compressed wave-shaped compression lines 1608 having a wave length w and an amplitude A. The compressed wave-shaped compression lines 1608 in the FIG. 16 pledget 1616 have a uniform wave shape with a constant amplitude A and wave length w.

Figure 17:
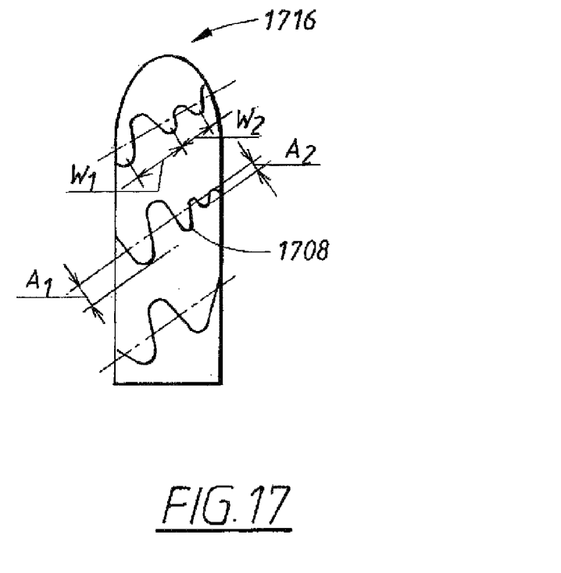
FIG. 17 shows a further example of how wave amplitude and wavelength are determined in a tampon where the wave-shaped compression lines have different wavelengths and amplitudes.

FIG. 17 shows an example of a compressed tampon pledget 1716 having a non-uniform wave shaped compression line 1708 with non-uniformly varying wave lengths $w_1$, $w_2$ and amplitudes $A_1$, $A_2$.

Figure 18:
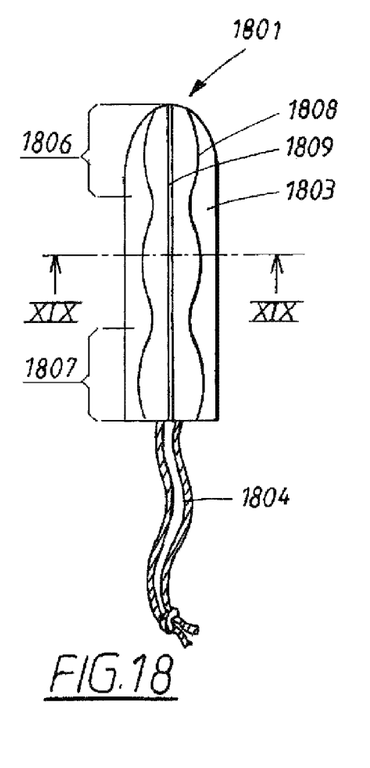
FIG. 18 shows a tampon having longitudinally extending compression lines made by different pressing methods.

The tampon 1801 in FIG. 18 has a first set of compression lines 1808 that are wave shaped and extend from the insertion end 1806 to the withdrawal end 1807 and a second set of straight compression lines 1809 that also extend from the insertion end 1806 to the withdrawal end 1807. The appearance of the tampon 1801 in FIG. 18 before use is like that of the tampon 1 in FIG. 1.

The first set of compression lines 1808 are formed by hot pressing and are more stable structures that withstands wetting without loosing definition to a higher degree than the second set of compression lines 1809. The second set of compression lines 1809 are cold pressed structures that become gradually obliterated as the tampon 1801 swells upon absorption of fluid.

Figure 19A:
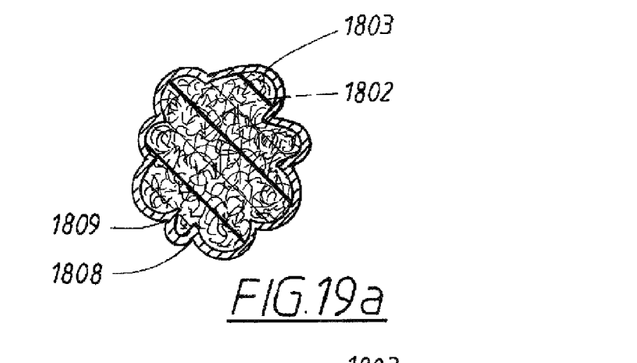
FIG. 19a shows a cross-section taken along the line XIX-XIX through the tampon in FIG. 18 when the tampon is in a partially expanded state.
Figure 19B:
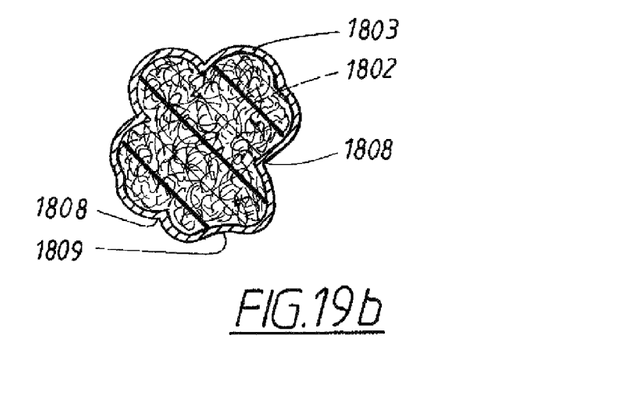
FIG. 19b shows a cross-section taken along the line XIX-XIX through the tampon in FIG. 18 when the tampon is in a fully expanded state.

FIG. 19a shows a cross section through the tampon 1801 in a partly expanded state after having absorbed some fluid and FIG. 19b shows the tampon 1801 in a fully expanded state when it has reached its full absorption capacity. The figures illustrate how the cold pressed less stable second set of compression lines 1809 are gradually obliterated as the tampon swells to its full capacity while the more stable hot pressed compression lines 1808 remain identifiable in the fully expanded tampon.

Figure 20:
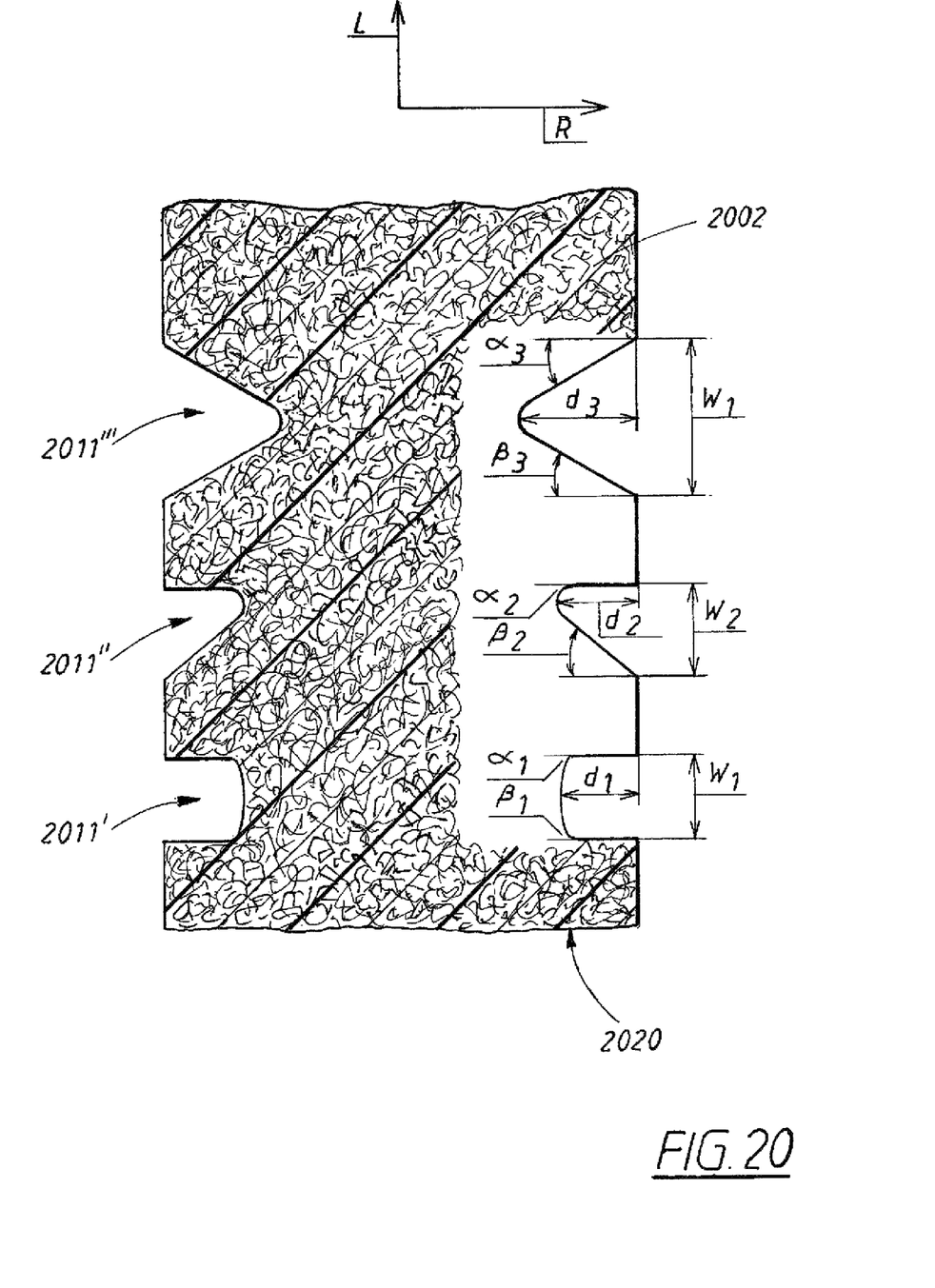
FIG. 20 shows the withdrawal end of a tampon having indentations impressed therein.
Figure 21A:
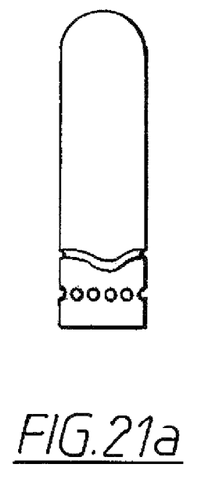
Figure 21B:
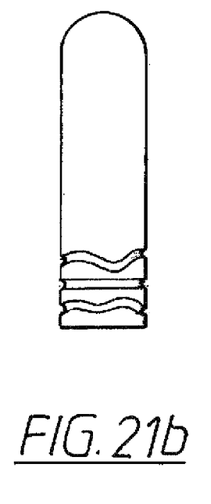
Figure 21C:
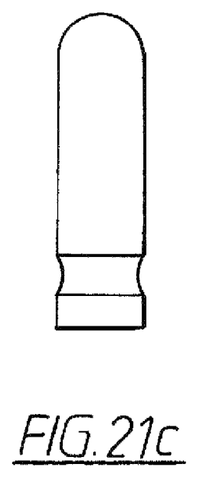
Figure 21D:
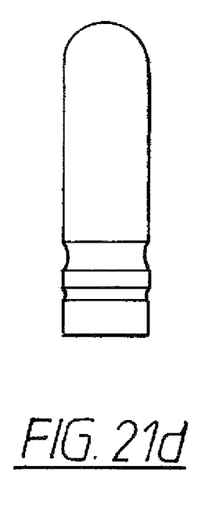
Figure 21E:
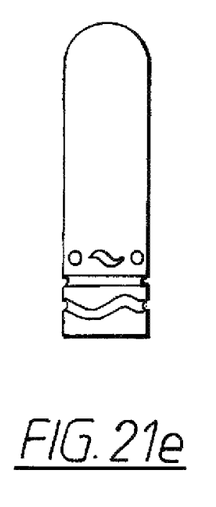
Figure 21F:
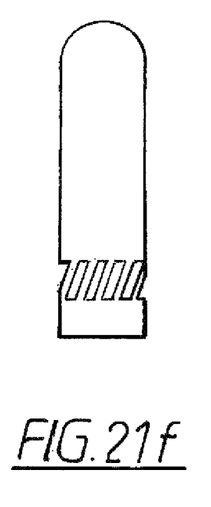

FIG. 20 shows a schematic representation of a withdrawal end of a tampon 2001 provided with indentations 2011', 2011'', 2011'''. FIG. 20 illustrates that the indentations may have different cross-sectional shapes, widths and depths. The depth, d, of the indentations from the tampon surface may be from 0.5 to 4 mm, preferably of from 1 to 2 mm. The indentations in FIG. 20 are line impressions that may be wave-shaped or straight with the impressed lines forming troughs or channels in the tampon absorption body 2002. The troughs or channels may have straight walls parallel to the radial direction R of the tampon. When the indentations 2011' have walls parallel to the radial direction R, the angles between the walls and the radial direction is 0° and the indentation has an approximately rectangular cross-section as shown in the indentation 2011' closest to the end surface 2020 of the tampon. Preferably, at least one of the walls are at an angle $\alpha$, $\beta$ to the radial direction R of the tampon, as shown in the second and third indentations 2011'' and 2011''' as seen from the end surface 2020. in the second indentation 2011'', the upper angle, $\alpha_2$ is 0° and the lower angle $\beta_2$ is approximately 40°. In the third indentation 2011''', the upper angle $\alpha_3$ and the lower angle $\beta_3$ are both approximately 30°. The angles $\alpha$, $\beta$, may be of from 0-60°. The indentations 2011', 2011'', 2011''' are shown to have rounded bottom surfaces. This is a preferred shape of the indentations for manufacturing reasons although planar bottom surfaces are also within the scope of the invention. The inclination of the walls may be equal with $\alpha=\beta$ or different with $\beta \neq \beta$ so that the trough may have a symmetrical or asymmetrical shape as desired.

The indentations 2011', 2011'', 2011''' in FIG. 20 have different depths, $d_1$, $d_2$, $d_3$, in the radial direction R. The depth of the indentations 2011', 2011'', 2011''' may be of from 0.5 mm to 4 mm, preferably of from 1 mm to 2 mm. the width $w_1$, $w_2$, $w_3$ of the indentations 2011', 2011'', 2011''' in the length direction L of the tampon may be of from 0.5 to 5 mm, preferably of from 1 to 4 mm.

The tampon pledgets shown schematically in FIGS. 21 a-f illustrate that the tampons may have indentations of different shapes, configurations and sizes. The only requirement for the indentations placed at the withdrawal end of the tampon is that they are arranged to form a radial constriction in the tampon absorption body at the withdrawal end. While still being absorbent, due to the smaller capillaries in the compact structure formed by the indentations, fluid flow past the indentations is slowed down so that fluid taken up by the tampon will have time to be distributed within the absorption body above the indentations. This leads to better utilisation of the absorbent material in the tampon.

Figure 22A:
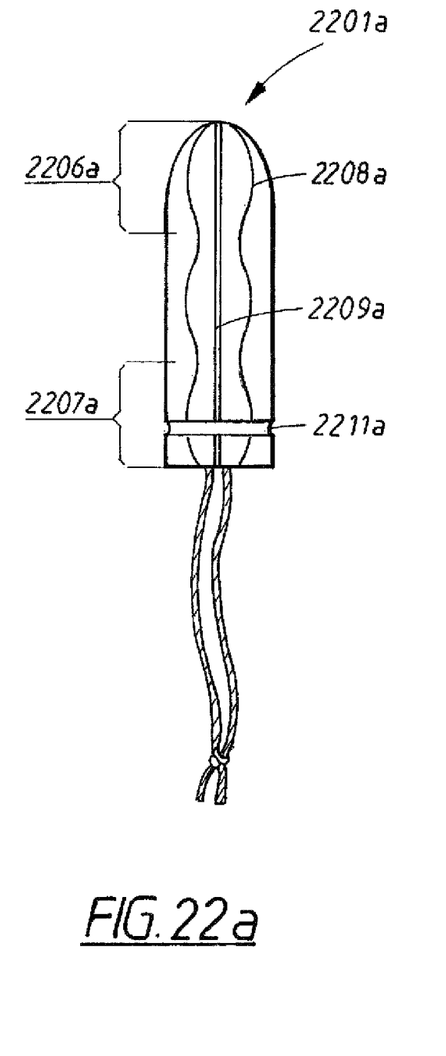
Figure 22B:
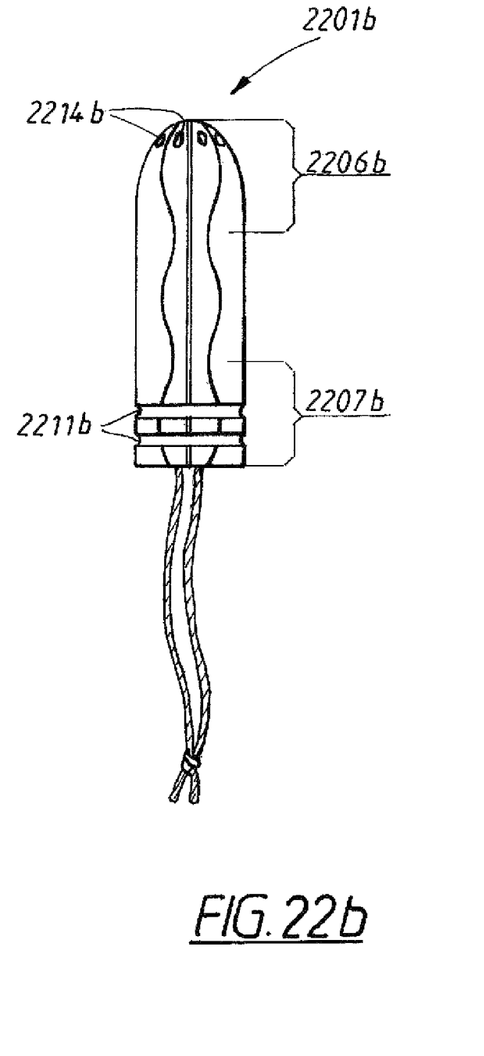

FIGS. 22a and 22b illustrate that the tampons may have combinations of the different compressed structures as disclosed herein. The tampon 2201a in FIG. 22a has wave shaped compression lines 2208a and straight compression lines 2209a in combination with a ring shaped indentation 2211a at the withdrawal end 2207a. The wave shaped compression lines 2208a have the same wave lengths and amplitudes but are arranged in a non-congruent pattern with the waves in neighbouring wave shaped compression lines 2208a being offset by half a wavelength. The compression lines 2208a, 2209a may have different impression depths between different compression lines or within one and the same compression line, as disclosed herein.

The tampon 2201b in FIG. 22b is similar to that in FIG. 22a, but has two indentations 2211b at the withdrawal end 2207b and dot compressions 2214b at the insertion end 2206b.

It is to be understood that the different wave shaped and straight compression lines, indentations and dot compressions shown and described herein may be used alone or in combination with each other. Accordingly, the invention shall not be considered to be limited to the specific combinations shown herein as the different shapes and functions of the compressions described herein may be freely combined within the scope of the invention.

The invention claimed is:

1. A compressed menstrual tampon comprising an elongated generally rod-shaped absorption body having an insertion end and a withdrawal end and having a withdrawal string extending from the withdrawal end, wherein the absorption body has at least two wave shaped compression lines extending continuously from the insertion end to the withdrawal end;

wherein an amplitude of each of the at least two wave shaped compression lines extends at least partially in a circumferential direction of the rod-shaped absorption body;

wherein the at least two wave shaped compression lines are arranged at least on an exposed outer surface of the rod-shaped body in a non-congruent pattern so that waves in neighbouring wave shaped compression lines are out of phase with each other; and wherein each of the compression lines forms a channel having two walls substantially in the radial direction of the tampon, the walls being at an angle to the radial direction of the tampon of from 0°-60°, each wall extends from an interior region of the absorption body to an exterior region of the absorption body, and wherein an interior edge of each wall of one of the compression lines is joined to an interior edge of the other wall of the one compression line.

2. A compressed menstrual tampon according to claim 1, wherein the at least two wave shaped compression lines are arranged in a non-congruent pattern.

3. A compressed menstrual tampon according to claim 1, wherein the absorption body comprises a mass of fibres.

4. A compressed menstrual tampon according to claim 1, wherein the absorption body comprises superabsorbent material.

5. A compressed menstrual tampon according to claim 1, wherein each wave shaped compression line has 1-6 full waves, each full wave comprising a wave crest and a wave trough.

6. A compressed menstrual tampon according to claim 5, wherein the amplitude of the waves is 0.3-5 mm.

7. A compressed menstrual tampon according to claim 5, wherein the wave length of the waves is 5-50 mm.

8. A compressed menstrual tampon according to claim 5, wherein the amplitude of the waves is 0.5-3 mm.

9. A compressed menstrual tampon according to claim 1, wherein the at least two wave shaped compression lines have a depth of from 1 to 6 mm as measured from the circumferential surface of the tampon.

10. A compressed menstrual tampon according to claim 9, wherein the at least two wave shaped compression lines have different depths along the length of the compression line.

11. A compressed menstrual tampon according to claim 1, wherein each wave shaped compression line has a uniform sinusoidal wave shape with equal wave length and equal amplitude and with the waves offset in relation to each other by half a wavelength.

12. A compressed menstrual tampon according to claim 1, wherein at least one of the at least two wave shaped compression lines has waves with different amplitudes.

13. A compressed menstrual tampon according to claim 1, wherein the tampon has 1-5 indentations in the form of line impressions at the withdrawal end.

14. A compressed menstrual tampon according to claim 13, wherein the distance from the withdrawal end surface to the edge of the first indentation as seen from the withdrawal end is 1-10 mm.

15. A compressed menstrual tampon according to claim 13, wherein the tampon has at least two indentations placed at an edge-to-edge distance from each other of from 1-7 mm.

16. A compressed menstrual tampon according to claim 13, wherein the indentations have a depth from the tampon surface of from 0.5 to 4 mm.

17. A compressed menstrual tampon according to claim 13, wherein the indentations have a depth from the tampon surface of from 1 to 2 mm.

18. A compressed menstrual tampon according to claim 13, wherein the indentations are wave-shaped or straight line impressions forming troughs or channels in the tampon absorption body, each trough or channel having two walls in the radial direction of the tampon, the walls being at an angle to the radial direction of the tampon of from 0°-60°.

19. A compressed menstrual tampon according to claim 18, wherein the tampon has at least one indentation wherein the angle between one of the walls and the radial direction of the tampon is equal to the angle of the other wall and the radial direction of the tampon.

20. A compressed menstrual tampon according to claim 18, wherein the tampon has at least one indentation wherein the angle between one of the walls and the radial direction of the tampon is different from the angle of the other wall and the radial direction of the tampon.

21. A compressed menstrual tampon according to claim 1, wherein the tampon has at least one dot compression placed at the insertion end.

22. A compressed menstrual tampon according to claim 21, wherein the at least one dot compression is made by hot compression.

23. A compressed menstrual tampon according to claim 21, wherein the interior edges are joined so as to form a rounded bottom.

24. A compressed menstrual tampon according to claim 1, further comprising a straight compression line between the at least two wave shaped compression lines arranged on the outer surface of the rod-shaped body.

25. A compressed menstrual tampon according to claim 1, wherein each of the at least two wave shaped compression lines includes at least two full waves.

* * * * *